US012383504B2

(12) United States Patent
Takubo

(10) Patent No.: US 12,383,504 B2
(45) Date of Patent: Aug. 12, 2025

(54) ACID RESISTANT BANDING SOLUTION FOR TWO PIECE HARD CAPSULES

(71) Applicant: Capsugel Belgium NV, Bornem (BE)

(72) Inventor: Takahisa Takubo, Auase (JP)

(73) Assignee: Capsugel Belgium NV, Bornem (BE)

(*) Notice: Subject to any disclaimer, the term of this patent is extended or adjusted under 35 U.S.C. 154(b) by 620 days.

(21) Appl. No.: 14/402,669

(22) PCT Filed: May 20, 2013

(86) PCT No.: PCT/IB2013/001423
§ 371 (c)(1),
(2) Date: Nov. 20, 2014

(87) PCT Pub. No.: WO2013/175303
PCT Pub. Date: Nov. 28, 2013

(65) Prior Publication Data
US 2015/0140084 A1    May 21, 2015

Related U.S. Application Data

(60) Provisional application No. 61/707,135, filed on Sep. 28, 2012, provisional application No. 61/649,549, filed on May 21, 2012.

(51) Int. Cl.
*A61K 9/48* (2006.01)
*A23L 33/10* (2016.01)
*A61K 31/167* (2006.01)
*A61K 47/10* (2017.01)
*A61K 47/46* (2006.01)

(52) U.S. Cl.
CPC ............ *A61K 9/4833* (2013.01); *A23L 33/10* (2016.08); *A61K 9/4858* (2013.01); *A61K 9/4866* (2013.01); *A61K 9/4883* (2013.01); *A61K 9/4891* (2013.01); *A61K 31/167* (2013.01); *A61K 47/10* (2013.01); *A61K 47/46* (2013.01); *A23V 2002/00* (2013.01)

(58) Field of Classification Search
None
See application file for complete search history.

(56) References Cited

U.S. PATENT DOCUMENTS

| 2,245,100 | A | * | 6/1941 | Bernstein | C09D 193/00 |
| | | | | | 106/222 |
| 2,924,920 | A | | 2/1960 | Margolis | |
| 3,071,513 | A | | 1/1963 | De Boer et al. | |
| 3,365,365 | A | | 1/1968 | Leonardo et al. | |
| 4,196,564 | A | | 4/1980 | Bodenmann et al. | |
| 4,478,658 | A | | 10/1984 | Wittwer | |
| 4,756,902 | A | | 7/1988 | Harvey et al. | |
| 9,452,141 | B1 | | 9/2016 | Chang et al. | |
| 2002/0114832 | A1 | * | 8/2002 | Herrmann | A61K 36/23 |
| | | | | | 424/461 |
| 2007/0212411 | A1 | * | 9/2007 | Fawzy | A61K 9/4808 |
| | | | | | 424/457 |
| 2008/0025966 | A1 | * | 1/2008 | Currie | A61K 31/40 |
| | | | | | 424/94.64 |
| 2011/0159093 | A1 | * | 6/2011 | Sheth | A61K 9/2081 |
| | | | | | 424/469 |
| 2013/0115285 | A1 | * | 5/2013 | Van Ness | A61K 47/34 |
| | | | | | 424/463 |
| 2017/0157058 | A1 | | 6/2017 | Chang et al. | |

FOREIGN PATENT DOCUMENTS

| CA | 2735050 A1 * | 2/2010 | ........... A61K 31/198 |
| EP | 0152517 | 8/1985 | |
| EP | 1752140 | 2/2007 | |
| EP | 1832282 * | 9/2007 | |
| EP | 3 178 473 | 6/2017 | |
| JP | S51-038413 | 3/1976 | |
| JP | S53-145907 | 12/1978 | |
| JP | S59-082311 | 5/1984 | |
| JP | S59-125566 | 7/1984 | |
| JP | S61-280422 | 12/1986 | |
| JP | H01-1178564 | 7/1989 | |
| JP | H09-216818 A | 8/1997 | |
| JP | 2000-139372 | 5/2000 | |
| JP | 2002-533380 | 10/2002 | |
| JP | 2004 018443 | 1/2004 | |
| JP | 2006-182771 | 7/2006 | |
| JP | 2008-201713 | 9/2008 | |
| JP | 2009-504630 A | 2/2009 | |
| JP | 2009-055850 | 3/2009 | |

(Continued)

OTHER PUBLICATIONS

Machine Translation of JP 2004 018443 A (Pigeon Corp; Sankyo Co) Jan. 22, 2004.*
International Search Report and Written Opinion from International application No. PCT/IB2013/001423, dated Aug. 12, 2013, 3pp.
Notification of Reasons for Refusal issued by Japan Patent Office for Japanese Application No. 2015-513290 on Feb. 7, 2017, 8 pages (with English translation).
Notice of Reasons for Rejection issued by Japan Patent Office on Oct. 2, 2018, for Japanese Application No. 2017-250755.

(Continued)

*Primary Examiner* — David J Blanchard
*Assistant Examiner* — Sarah J Chickos
(74) *Attorney, Agent, or Firm* — Klarquist Sparkman, LLP

(57) ABSTRACT

The present disclosure relates to acid resistant banding solutions for two piece hard capsules, and methods of making the same. The present disclosure also relates, in part, to a method for banding such capsules which provides an acid resistant seal between the capsule parts and achieves an increased acid resistance in vitro. The instant disclosure further relates to a capsule sealing solution formula that comprises shellac ink or shellac ink vehicle component.

15 Claims, 1 Drawing Sheet

(56) References Cited

FOREIGN PATENT DOCUMENTS

| | | |
|---|---|---|
| JP | 2010-065023 | 3/2010 |
| JP | 2015-502923 A | 1/2015 |
| TW | 200520790 | 7/2005 |
| TW | 1587880 | 10/2016 |
| WO | WO 00/38655 | 7/2000 |
| WO | WO 2005/020937 | 3/2005 |
| WO | WO 2007/020529 | 2/2007 |
| WO | WO 2011/036601 | 3/2011 |
| WO | WO 2011/100643 | 8/2011 |

OTHER PUBLICATIONS

Notice of Reasons for Rejection issued by Japan Patent Office on May 14, 2019, for Japanese Application No. 2017-250755.
European Office Action issued by European Patent Office on Dec. 14, 2018, for European Application No. 13736640.7.

* cited by examiner

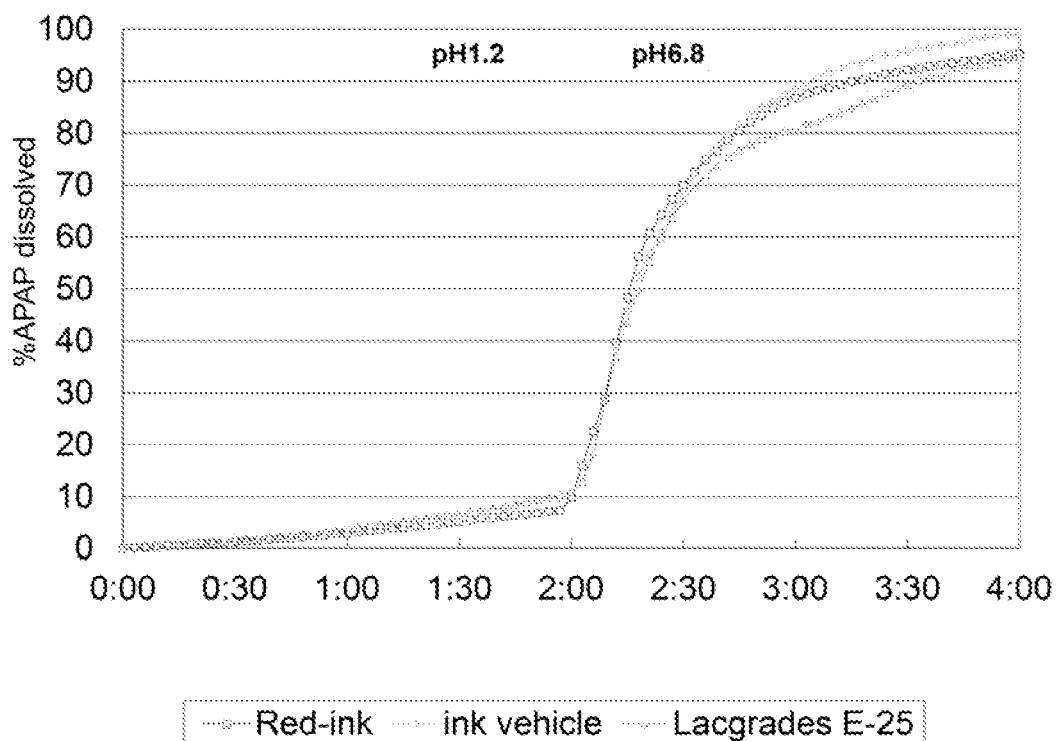

ACID RESISTANT BANDING SOLUTION FOR TWO PIECE HARD CAPSULES

CROSS REFERENCE TO RELATED APPLICATIONS

This is the U.S. National Stage of International Application No. PCT/IB2013/001423, filed May 20, 2013, which was published in English under PCT Article 21 (2), which in turn claims the benefit of U.S. Provisional Application No. 61/649,549, filed May 21, 2012, and claims further benefit of U.S. Provisional Application No. 61/707,135, filed Sep. 28, 2012. The prior applications are incorporated herein in their entirety.

The present application claim priority to U.S. Provisional Application No. 61/649,549 filed May 21, 2012, and to U.S. Provisional Application No. 61/707,135 filed Sep. 28, 2012.

The present disclosure relates to acid resistant banding solutions for banding two piece hard capsules, and use of such capsules particularly but not exclusively for oral administration of pharmaceuticals, veterinary products, foods and dietary supplements to humans or animals.

The two piece hard capsules are the oral dosage form preferred by patients, and traditionally made with gelatin for more than a century. Over the past twenty years, new types of hard capsules have been developed with alternative raw materials, mainly with hypromellose (hydroxypropyl methyl cellulose) and pullulan. All these capsules are of the immediate release type or are designed for releasing their content in the stomach rapidly after administration.

Efforts were made to impart a specific functionality to the hard capsules. The most successful example is the gastric resistant hard capsules which can protect the content from the acid conditions (e.g., within the stomach), with a delayed release or an intestinal release. Generally, such capsules are utilized in the pharmaceutical and food industries to hold pharmaceutically active materials such as medicines, vitamin preparations and other edibles, both solid and liquid, and protect them from the acid conditions in the stomach.

Delayed, sustained or extended release capsules resistant to the acid conditions of the stomach were developed early on using gelatin insolubilization by treatment with formaldehyde. See. e.g., Ridgway et. al., *Hard Capsule Development & Technology*, The Pharmaceutical Press, 1978, p. 11.

With the development of capsule coating technology, the enteric hard capsules ("enteric coated capsules") became more popular on the pharmaceutical market. See, e.g., Ridgway et. al., *Hard Capsule Development & Technology*, The pharmaceutical Press, 1978, pp. 229 to 232.

In both above cases, the capsule itself is of immediate release, and its acid resistance is achieved by a post-manufacturing treatment of the capsule, generally after filling at the pharmaceutical company site.

More recently Capsugel has developed an intrinsically acid resistant hard capsule (DRCAPS™ acid resistant capsules). This capsule is made with an acid resistant formula, and consequently the capsule shell is acid resistant without any post-fill coating treatment.

Further evaluation of the DRCAPS™ delayed release capsules revealed that under certain conditions there remained a risk for the two parts of the capsule, body and cap, to separate under the mechanical stress of in vitro dissolution tests, notably during certain in vitro acidic conditions disintegration testing. Similarly, there is always a risk of diffusion of dissolution medium into the closed capsule or of content from the capsule through the gap between body and cap. In vivo, this risk of capsule separation could result in dissolution or disintegration of the final dosage form capsule and premature release of the drug.

Consequently there is a need to develop a way to effectively prevent the body-cap separation and the diffusion through the gap during the in vitro tests, and thus to improve the in vivo acid resistance performance of the final dosage form.

A number of solutions to decrease the leakage through the body-cap gap have been developed. For example, the hard gelatin capsule banding with a gelatin solution is commonly used to prevent the content leakage during storage.

Another method to decrease leakage is to seal the cap and the body of the capsule directly to each other by means of a "sealing fluid". See e.g., U.S. Pat. Nos. 3,071,513; 2,924,920; FR 2,118,883, EP 0152517; U.S. Pat. No. 4,756,902; FR 2 118883; EP 0152517; U.S. Pat. No. 4,756,902.

However, all the above-described banding solutions do not exhibit appropriate acid resistance, and therefore would dissolve in acid media during in vitro testing, and in the stomach. Thus there is a need to develop a safe and effective method for acid resistant capsules to prevent the body-cap separation and the diffusion through the gap.

Furthermore, the development of hypromellose (hydroxypropyl methyl cellulose) capsules created a need to adapt the composition of the banding solution to the polymer properties (available from Capsugel as PLANTCAPS™). See, e.g., WO2007/020529; WO2011/036601.

The risks of separation of the capsule body and cap discussed above in connection with DRCAPS™ delayed release capsules are also applicable to other types of two piece hard capsules such as immediate release capsules.

Accordingly, one aspect of the present disclosure provides acid resistant banding solutions for banding acid resistant two piece hard capsules, wherein said capsules comprise telescopically engaged capsule parts and are endowed with improved acid resistance properties.

In a preferred aspect, the present disclosure provides an acid-resistant banding composition comprising an ink vehicle solution for use with acid resistant and with immediate release two piece hard capsules.

In yet another aspect, the present disclosure provides acid resistant banding solutions for banding immediate release two piece hard capsules.

In another aspect, the present disclosure provides a method for banding such capsules which provides an acid resistant seal between the capsule parts and achieves an increased acid resistance in vitro.

In a further preferred aspect, the present disclosure relates to banding solutions for acid resistant and immediate release capsules, and methods thereof, taking advantage of conventional banding techniques and equipment. See, e.g., Podczeck et al., *Pharmaceutical Capsules*, Pharmaceutical Press $2^{nd}$. Ed. pp. 182-183.

As used in the present disclosure, the following words, phrases, and symbols are generally intended to have the meanings as set forth below, except to the extent that the context in which they are used indicates otherwise.

As used herein, "optional" or "optionally" means that the subsequently described event or circumstance may or may not occur, ad that the description includes instances where the event or circumstance occurs and instances in which it does not.

The term "about" is intended to mean approximately, in the region of, roughly, or around. When the term "about" is used in conjunction with a numerical range, it modifies that range by extending the boundaries above and below the numerical values set forth. Unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Unless otherwise indicated the term "acid resistant two piece hard capsules" refers to two piece hard capsules described as acid resistant or manufactured from acid resistant formulas or obtained by appropriate treatment post capsule manufacturing. Acid resistant capsules are typically sustained, delayed or extended release capsules that release the contained active ingredient at a sustained and controlled release rate over a period of time (e.g., hours).

Unless otherwise indicated, the term "immediate release two piece hard capsules" refers to two piece hard capsules in which the active ingredient in the capsule is released within a small period of time, typically in the stomach and typically within less than 30 minutes following ingestion.

As used herein, the term "vehicle" is intended to connote any of various media acting usually as solvents, carriers, or binders for active ingredients or pigments. More particularly, the term "ink vehicle" is intended to connote an ink without colorants or coloring agent.

Further aspects, features and advantages of the present disclosure will be better appreciated upon a reading of the description.

DESCRIPTION OF THE FIGURES

FIG. 1 illustrates results by the dosage method of capsules filled with APAP and banded with red ink, and ink vehicle, and evaluated to determine the % of APAP dissolved over a period of up to 240 minutes by USP dissolution test method.

DESCRIPTION

In one embodiment, the present disclosure provides a banding composition for hard capsules comprising an ink vehicle comprising a shellac, at least one alcohol, and at least one surfactant.

In one embodiment, the hard capsules are acid resistant capsules.

In another embodiment, the hard capsules are immediate release capsules.

In another embodiment, the banding composition according to the present disclosure may further comprise pharmaceutically acceptable or food acceptable alkali-like ammonia water and/or alkaline base.

In another embodiment, the banding composition according to the present disclosure may further comprise at least one pharmaceutically acceptable or food acceptable plasticizer, including esters such as ethyl acetate, and polyols such as glycerin, ethylene glycol and propylene glycol.

In another embodiment, the banding composition according to the present disclosure may further comprise at least one pharmaceutically acceptable or food acceptable coloring agent.

In a further embodiment the present disclosure provides a banding composition for hard capsules comprising a shellac or ink vehicle solution.

In accordance with the aforementioned embodiment, the ink vehicle solution formula comprises shellac in the range of about 10 wt. % to about 60 wt. %, and more preferably in the range of from about 20 wt. % to about 45 wt. % at least one alcohol in the range of about 15 wt. % to about 70 wt. %; at least one surfactant in the range of about 0.1 wt. % to about 5 wt. %, and more preferably in the range of from about 0.5 wt. % to about 3 wt. %; ammonia water in the range of from about 0 wt. % to about 8 wt. %, and more preferably in the range of from about 0 wt. % to about 5 wt. %; rosin in the range of about 0 wt. % to about 20 wt. %, and more preferably in the range of from about 5 wt. % to about 15 wt. %; and colorant or coloring agent (which encompasses pigments and/or dyes) in the range of about 0 wt. % to about 50 wt. %, and more preferably in the range for from about 0 wt. % to about 10 wt. %, based on the total weight of the solution.

It has been found by the instant inventors that after the aforementioned solution dries and the alcohol evaporates, the banding solution comprises about 0% alcohol, ammonia water in the range of from about 0-10 wt. %, shellac in the range of about 20-95 wt. %, rosin in the range of about 0-35 wt. %, surfactant in the range of about 0.1-10 wt. %, and colorant or coloring agent in the range of about 0-70 wt % based on the total weight of the solution. In one embodiment, the capsule according to the present disclosure comprises a dry sealing composition comprising shellac in an amount ranging from about 20 wt % to about 95 wt %, rosin in an amount less than 35 wt %, and at least one surfactant in an amount ranging from about 0.1 wt % to about 10 wt % based on the total weight of the composition.

The present disclosure also provides an effective acid resistant banding of hard capsules even with low band thickness, such as lower than 10 mg, or even lower than 5 mg for the dry band weight for size 1 capsules.

In accordance with the instant disclosure the ink utilized in the banding solution may comprise any food and/or pharmaceutical grade ink as known to those of ordinary skill in the art. Advantageously, the ink for use as a vehicle in the solution formula is without pigments. The present disclosure is not, however, limited to an ink vehicle without pigments. A list of various ink vehicle solutions investigated in accordance with the instant disclosure is shown in FIG. 1.

Optionally, certain embodiments include treatment of the banded capsules post-banding with one or more lubricants, including not limited to talc and stearate compounds such as calcium stearate.

Non-limiting examples of pigments in accordance with the instant disclosure include both organic and inorganic pigments as well as lakes and dyes.

Organic pigments include, for example, FD&C Blue No. 1 and 2, D&C Blue No. 4 and 9. FD&C Green No. 3. D&C Green No. 5, 6 and 8, D&C Orange No. 4, 5, 10 and 11. FD&C Red No. 3, 4 and 40, D&C Red No. 6, 7, 17, 21, 22, 27, 28, 30, 31, 33, 34, 36, and 39, D&C Violet No. 2, FD&C Yellow No. 5, 6 and 7, D&C Yellow No. 8, 10 and 11. Also included are beta-carotene, Canthaxanthin. Caramel, Carnine from Cochineal extract, Copper chlorophyllin salt and vegetable carbon. (See USP Dyes, Handbook of Pharmaceutical Excipients, $5^{th}$ ed 2007).

Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate, cobalt aluminate; and mixtures thereof. Other suitable colorants include ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and mixtures thereof.

Preferred pigments in accordance with certain embodiments include titanium dioxide ($TiO_2$), iron oxide, dyes, and mixtures thereof.

Shellac as used herein is obtainable from the secretion of lac insects (Kerrialacca or Lacciferlacca), and occurs as a stiff resin having an average molecular weight of approx. 1000 g/mol. It is made up predominantly of partly unsaturated hydroxycarboxylic acids that are present either as esters with one another or as a lactone. The principal components are aleuritic acid (aleuric acid, 9,10,16-trihydroxypalmitic acid) with up to approx. 32 wt % shellolic acid.

Exemplary alcohols for use in the solution formulas in accordance with certain embodiments include, but are not limited to, branched or straight chain alcohols of 2-6 carbons, and combinations of alcohols. In certain embodiments in accordance with the instant disclosure, the alcohols include ethanol, 95% ethanol, n-butyl alcohol, and mixtures thereof.

Alkali compounds for stabilizing shellac in solution in accordance with certain embodiments include, but are not limited to, ammonia water, hydroxide, carbonate compounds, and mixtures thereof.

Rosin is a well-known, commercially available material. In terms of its chemical structure, it is mainly a mixture of $C_{20}$, tricyclic fused-ring, mono-carboxylic acids, typified by abietic acid. Individually, these monocarboxylic acids are referred to as resin acids. In combination, they are commonly referred to as rosin. Rosin can be obtained from many sources, and can have a wide range of purities. For example, wood rosin is obtained from *Pinus* stumps after harvesting the stumps, chipping the stumps into small chips, extracting the chips with hexane or higher-boiling paraffins, and distilling the hexane or paraffin and fatty acids to yield wood rosin. Gum rosin is the name given to rosin that is obtained alter scoring a pine tree, collecting the exudate sap, and then distilling away the volatile components and most of the fatty acids. Rosin is typically characterized by its acid number, and rosins having acid numbers ranging from about 150 to about 200 are embodiments according to the disclosure disclosed herein. As recited above, the rosin typically contributes about 0 wt. % to about 20 wt. % to the banding solution formula for scaling the capsules.

The ink component in accordance with the solution formula favorably contains a surfactant. A non-limiting list of surfactants that can be utilized in the solution formula in accordance with the present disclosure include natural or synthesized surfactants, and particularly non-ionic surfactants. Surfactants in accordance with certain embodiments include glycerin fatty acid esters and sorbitan fatty acid esters, and mixtures thereof.

Non-limiting examples are offered herein below to clarify the disclosure and are not intended to limit the scope of the present claims. The acid resistant capsules used in the banding examples are DRCAPS™ of size 0, natural transparent (N.T.) type, and can be applied to any size of DRCAPS™ capsules. The banding solutions of the present disclosure can be applied to any two piece hard capsules with acid resistance performance. DRCAPS™ are manufactured from non-animal cellulose polymers, specifically hypromellose (hydroxypropyl methyl cellulose).

While acid resistant banding solutions of the instant disclosure have been described with respect to acid resistant hard capsules fabricated from hypromellose, the instant disclosure is not limited to hypromellose capsules and this disclosure contemplates capsules fabricated from any suitable polymers or film-forming aids well known to those of ordinary skill in the art including, but not limited to, polyacrylates, polymethacrylates, polyvinylpyrrolidone, poly(vinyl acetate), various starches, corn products such as amaizo, amylose and zein, pectin, alkoxylated celluloses, polyesters, polyethers, proteins, nucleic acids, albumin, gelatin, pullulan, chitin, chitosan, agar, starch, collagen, dextran and modified dextrans, polysaccharides, polylactide/polyglycolide, polyalkylcyanoacrylates, polyacrylamide, polysorbates, polyethylene ethers, polyethylene esters, polyoxyethylene/polyoxypropylene block polymers, cellulose acetophthalate, hydroxypropylmethyl cellulose, cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, cellulose acetate butyrate, methyl cellulose, ethyl cellulose, hydroxyethyl cellulose, propyl cellulose, hydroxypropyl cellulose, lower-substituted hydroxypropyl cellulose, and carboxymethyl cellulose.

The instant disclosure also contemplates the addition of or inclusion of other ingredients in the fabrication of the above-described hard capsules, such as for example but not limited to, film forming aids (e.g., plasticizers), dispersants, emulsifiers, binders, thickeners, fillers, solubilizers, gelling agents (e.g., carageenan, guar gum, xanthan gum and the like), lubricants, glidants, excipients and other commonly incorporated additives well known to those of ordinary skill in the art.

Suitable plasticizers include, but are not limited to, glycerin, sorbitol, propylene glycol, polyethylene glycols (e.g., PEG 400 or 900), triacetin, acetylated monoglyceride, citrate esters, phthalate esters, and mixtures thereof.

Suitable gelling agents include, but are not limited to, carrageenans; gums such as gellan, xanthan, locust bean, arabic or guar gum; pectin; chitosan; alginates, and mixtures thereof.

Suitable film-forming aids include, but are not limited to, additional cellulose derivatives displaying compatibility with the main polymer used for capsule manufacturing such as HPC (hydroxypropyl cellulose), EC (ethyl cellulose), MC (methyl cellulose), HPMCAS (hydoxypropylmethyl cellulose acetate succinate), HPMCP (hydroxypropylmethyl cellulose phthalate); coalescents or surfactants such as sorbitan esters; polyoxyethylene, polyoxypropylene and mixtures of thereof; glycerol; polyvinyl acetate derivatives; and mixtures thereof.

Suitable lubricants or glidants or anti tacking agents, include for example, fumed silica or colloidal silicon dioxide such as Aerosil 200 (Evonik Industries, USA) or Cab-O-Sil (Cabot Corp., USA), talc, bentonite, stearic acid, magnesium stearate, calcium stearate, sodium stearyl fumarate, polyethylene glycol, sodium lauryl sulphate, and mixtures thereof.

Non-limiting examples of ingredients that may be filled into hard capsule embodiments include commonly known powders, granules and tablets, and also alcohols, including polyhydric alcohols such as stearyl alcohol, cetanol, and polyethylene glycol (PEG) 400, 600, 800, 1000, 1500, 2000, 3000, 4000, 6000, 8000, and 20000; fats and oils such as sesame oil, soybean oil, peanut oil, corn oil, hardened oil, paraffin oil and white beeswax; and fatty acids and fatty acid derivatives such as stearic acid, palmitic acid, myristic acid, triethyl citrate, triacetine and middle-chain fatty acid triglycerides, and mixtures thereof. Physiologically active substances that may be used to fill capsules produced according to the embodiments herein for drug and food applications are not subject to any particular limitation, so long as they are non-toxic.

The capsules may be filled with a very broad range of active ingredients, i.e., a pharmaceutical ingredient, a drug, or a nutritional supplement, or mixtures thereof, which include but are not limited to vitamins, nutritional supplements, antipyretics, analgesics, anti-inflammatory agents, antiulceratives, cardiotonics, anticoagulants, hemostatics, bone resorption inhibitors, vascularization inhibitors, antidepressants, antineoplastics, antitussive expectorants, muscle relaxants, anticonvulsants, antiallergics, antiarrhythmics, vasodilators, hypotensive diuretics diabetes medications, antitubercular agents, hormones, narcotic antagonists, and combinations thereof.

Non-limiting examples of suitable vitamins that may be filled into the capsules include vitamin A, vitamin B1, vitamin B2, vitamin B6, vitamin B12, nicotinamide, calcium pantothenate, vitamin C, vitamin D2, vitamin E, vitamin K, and mixtures thereof.

Nutraceutical products or nutritional supplements according to certain embodiments are typically food or food products that are believed to provide health and medical benefits, including the prevention and treatment of disease. Non-limiting examples of nutraceutical products that may be filled into the capsule include artichoke, bilberry, bioflavonoid, boswella, bupleurium, chamomile, chlorophyll, cranberry, damiana, echinacea, essiac, garcinia cambogia, garlic, germaniun, ginger, gingko, ginseng, goldenseal, grape seed, green tea, hawthorne berry, hesperidin, hops, horse chestnut hydrangea, hypericum, indole-3-carbinol, licorice, lycopene, nettle root, peppermint, periwinkle, policosanol, psyllium, pygeum, quercetin, raspberry, resveratrol, rutin, sassafras, saw palmetto, silymarin, tribulus terestris, turmeric, valerian, wild yarn, and their nutraceutically acceptable salts, ethers, esters, acid, or other derivatives; as well as mixtures and combinations thereof.

The fill substance comprises active ingredients, i.e., a pharmaceutical ingredient, a drug, a nutraceutical, a nutritional supplement, and/or mixtures thereof which may be combined with any acceptable excipients known in the art, including but not limited to one or more diluents, binders, disintegrants, and/or mixtures thereof.

Suitable diluents include, but are not limited to, pharmaceutically acceptable inert fillers such as microcrystalline cellulose, lactose, dibasic calcium phosphate, saccharides, and/or mixtures of any of the foregoing. Examples of diluents include microcrystalline cellulose such as Avicel PH 12, Avicel PH 101 and Avicel PH 102 (FMC Biopolymer, U.S.A.); lactose such as lactose monohydrate, lactose anhydrous and Phamtatose DCL 21; dibasic calcium phosphate such as Emconpress; mannitol (J. Rettenmaier & Söhne GmbH+Co.KG, Germany); starch; sorbitol; fructose; sucrose; glucose, and mixtures thereof. Suitable binders include, but are not limited to, polyethylene glycols such as PEG 6000 cetostearyl alcohol; cetyl alcohol; polyoxyethylene alkyl ethers polyoxyethylene castor oil derivatives; polyoxyethylene sorbitan fatty acid esters; polyoxyethylene stearates; poloxamers; waxes, alginic acids and salts thereof; HPC (hydroxypropyl cellulose); HPMC (hydroxypropylmethyl cellulose); methylcellulose; maltodextrin and dextrin; povidone; gums; starch and modified starches.

Suitable disintegrants include, but are not limited to, sodium starch glycolate such as EXPLOTAB® (J. Rettenmaier & Söhne GmbH+Co.KG, Germany); crospovidone, such as Kollidon CL (BASF, Gemany). Polyplasdone XL (ISP, USA), sodium carboxymethylcellulose, sodium croscarmellose such as AcDiSol (FMC Biopolymer, USA) and starch. Suitable thickeners include, but are not limited to, cellulose derivatives such as carboxymethylcellulose such as blanose, polysaccharides or gums used in appropriate proportions, and mixtures thereof. Procedures for the banding of hard shell capsules are known in the art. The instant disclosure contemplates a method of banding two-piece hard capsules using the acid banding composition as described in accordance with the instant disclosure. In certain embodiments using methods well known in the art, capsules are sealed after filling in the overlapping region of capsule body and cap by commonly known sealing techniques like handing or applying a sealing liquid and/or heat to the gap between capsule body and cap. Methods of sealing or banding two piece hard capsules, as well as apparatuses for sealing and banding are disclosed, for example, in U.S. Pat. Nos. 8,181,425; 7,229,639; 7,094,425; 5,054,208; 4,940, 499; 4,922,682; 4,761,932 and 4,734,149, all of which are incorporated by reference herein.

EXAMPLES

The following examples describe specific aspects to illustrate the disclosure and provide a description of the present compositions and present methods for those of skill in the art. The examples should not be construed as limiting the disclosure, as the examples merely provide specific methodology useful in understanding and practice of the disclosure and its various aspects.

Example 1

Banding DRCAPS™ with Ink Vehicle Solution

DRCAPS™ acid resistant capsules were filled with APAP (N-acetyl-p-aminophenol, the active compound of acetaminophen) and sealed with red ink and the ink vehicle solutions as shown below in Table 1. The banded capsules filled with APAP were tested using the USP disintegration method in pH 1.2 media and evaluated by the dosage approach, which measures the % of APAP dissolved after a 2 hour-dissolution test at pH 1.2. FIG. 1 presents the results by the dosage method of banded capsules filled with APAP and evaluated to determine the % of APAP dissolved over a period of up to 240 minutes by USP dissolution test method.

Using DRCAPS™ acid resistant capsules filled with corn starch and sealed with the 100% shellac-alcohol solution (as a base-line). Red-ink, and the ink vehicle solutions as shown in Table 1, the banded capsules filled with corn starch were tested using the JP disintegration method (i.e., 120 min) in pH 1.2 media and evaluated by the dosage approach, which measures capsule's disintegration after 2 hours disintegration test at pH 1.2. Table 2 presents the results by the dosage method of banded capsules filled with Corn starch and evaluated to determine by visual observation of capsule's disintegration over a period of up to 120 minutes by JP disintegration test method.

TABLE 1

| | Shellac solution (Lacgrades E-25, Japan Shellac Industries, Ltd.) | Red ink | Ink vehicle |
|---|---|---|---|
| Ethanol | 75% | 27.1% | 58.4% |
| n-butyl alcohol | — | 27.1% | — |
| Shellac | 25% | 34.0% | 29.5% |
| Rosin | — | — | 7.5% |
| Water | — | — | 3.1% |
| Sorbitan fatty acid of ester | — | 1% | 1% |
| Glycerin fatty acid of ester | — | 0.5% | 0.5% |
| 28% ammonia water | — | 2.3% | — |
| Red iron oxide as pigment | — | 8% | — |
| Total | 100% | 100% | 100% |

TABLE 2

| | Number of disintegrated capsules after T = 120 min in pH 1.2 solution (no sinker, no disk used, n = 12 capsules). |
|---|---|
| Shellac solution Lacgrades E-25) | 4/12 |
| Red-ink | 0/12 |
| Ink vehicle | 0/12 |

Example 2

Banding Gelatin, Pullulan, and HPMC Capsules with Ink Vehicle Solution

Using the shellac/ink vehicle solution shown in Table 3, banding for liquid filled capsules was investigated. This provided for easy observation of the banding quality for each capsule material.

TABLE 3

| | |
|---|---|
| Ethanol | 58.4% |
| Shellac | 29.3% |
| Rosin | 7.5% |
| Water | 3.1% |
| Sorbitan fatty acid ester | 1.0% |
| Glycerin fatty acid ester | 0.5% |
| Total | 100% |

Capsules (n=100) were filled with "hot sesame oil" (low viscosity red color oil for food) and then banded by shellac ink vehicle solution using a banding machine. After drying, the banded capsules were stored in vacuum chamber of 250 mbar pressure (about ¼ atm, 1 atm=1013 mBar) for 20 minutes and then visually inspected to count the number of leaked capsules.

As shown in Table 4, the ink vehicle banding worked well with the gelatin capsules, the pullulan capsules (PLANTCAPS™ pullulan capsules from Capsugel), the HPMC capsule (VCAPS® Plus hydroxypropylmethyl cellulose capsules from Capsugel) and the HPMC capsules having gelling agents (VCAPS® hydroxypropyl methyl cellulose capsules from Capsugel).

TABLE 4

| Capsule Batch | Capsule | Capsule Supplier | Shell Material | Mold bar type | Size # | Filled oil dose (micro L | Leak result by visual after 250 mbar- 20 min depression |
|---|---|---|---|---|---|---|---|
| 223141 | Gelatin capsule | Capsugel | Gelatin | ND Licaps | 2 | 300 | 0/100 capsules |
| 228361 | VCAPS ® Plus | Capsugel | HPMC | ND Licaps | 2 | 300 | 0/100 capsules |
| 218921 | PLANTCAPS ® | Capsugel | Pullulan | ND Licaps | 2 | 300 | 0/100 capsules |
| 53173321 | DRCAPS ® | Capsugel | HPMC | Coni-Snap | 1 | 300 | 0/100 capsules |
| — | Quali-V | Qualicaps | HPMC | — | 1 | 300 | 0/100 capsules |

Ink vehicle viscosity can be adjusted by changing the amount of solvent. This provides for excellent banding quality using a banding machine. Table 5 provides a comparison of ink vehicles having different viscosities (ink vehicles A and B). Numbers in the table indicate composition % before and after drying.

TABLE 5

| | Ink (white) | | Ink vehicle-A (ink without pigment) | | Ink vehicle-B (high viscosity) | |
|---|---|---|---|---|---|---|
| | Solution | ← Dried | Solution | ← Dried | Solution | ← Dried |
| Viscosity [mPa s] | 81 | — | 34 | — | 550 | — |
| Shellac | 17.7 | 28.1 | 29.5 | 76.6 | 43.5 | 77 |
| Rosin | 4.5 | 7.1 | 7.5 | 19.5 | 11 | 19.5 |
| 95% Ethyl alcohol | 36.9 | 0 | 61.5 | 0 | 43.5 | 0 |
| TiO2 | 40 | 63.3 | 0 | 0 | 0 | 0 |
| Glycerin fatty acid ester | 0.3 | 0.5 | 0.5 | 1.3 | 0.7 | 1.8 |
| Sorbitan fatty acid ester | 0.6 | 1.0 | 1 | 2.6 | 1.3 | 3.7 |
| Total | 100 | 100 | 100 | 100 | 100 | 100 |

Example 3

Rosin Free Formula

Banding of hard capsules was also performed with a banding solution comprising ethanol 59.9 wt %, shellac 37 wt %, and water 1.6% (as in ethanol), sorbitan fatty acid of ester 1%, and glycerin fatty acid ester 0.5%. The capsules performed similarly with or without rosin on both dissolution and disintegration tests. Rosin-free compositions for shellac banding are of particular interest in some embodiments where the filled powders are "living probiotics."

Example 4

Post-Banding Treatment

The length of time for drying of the banded capsules may be adjusted according to the practical requirements of handling the dosage forms and the characteristics of the banding solution. We applied the lubricants talc or calcium stearate powders so as to speed the drying process and decrease sticking while the banding was not yet completely dried.

The content of all patents, patent applications, published articles, abstracts, books, reference manuals and abstracts, as cited herein are hereby incorporated by reference in their entireties to more fully describe the state of the art to which the instant disclosure pertains.

It should be understood that the foregoing description is only illustrative of the present disclosure. Various alternatives and modifications can be devised by those skilled in the art without departing from the instant disclosure. Accordingly, the present disclosure is intended to embrace all such alternatives, modifications and variations that fall within the scope of the appended claims.

What is claimed is:

1. An acid resistant band formed from an acid resistant banding composition, wherein the acid resistant band comprises from about 20 wt % to about 95 wt % shellac based on the total weight of the acid resistant banding composition, wherein the acid resistant band is formed on a two-piece hard capsule and is formed only at a juncture of a telescopically engaged cap and body of the two-piece hard capsule.

2. The acid resistant band according to claim 1, further comprising rosin, a plasticizer, or any combination thereof.

3. The acid resistant band according to claim 1, wherein the acid resistant band further comprises a surfactant.

4. The acid resistant band according to claim 1, wherein the acid resistant band comprises a surfactant present in an amount ranging from about 0.1 wt % to about 10 wt % based on the total weight of the acid resistant banding composition.

5. The acid resistant band according to claim 4, wherein the surfactant is selected from glycerin fatty acid esters, sorbitan fatty acid esters, and mixtures thereof.

6. The acid resistant band according to claim 1, further comprising ammonia water.

7. The acid resistant band according to claim 2, wherein the acid resistant band comprises rosin and the rosin is present in an amount less than about 35 wt % based on the total weight of the acid resistant banding composition.

8. The acid resistant band according to claim 3, wherein the surfactant is selected from glycerin fatty acid esters, sorbitan fatty acid esters, and mixtures thereof.

9. A sealed two-piece hard capsule comprising:
   a telescopically engaged cap and body forming a two-piece hard capsule shell;
   an acid resistant band formed only at the juncture of the telescopically engaged cap and body, wherein the acid resistant band is formed from an acid resistant banding composition and comprises about 20 wt % to about 95 wt % shellac based on the total weight of the acid resistant banding composition;
   wherein the two piece hard capsule shell is formed from a material selected from polyacrylates, polymethacrylates, polyvinylpyrrolidone, poly (vinyl acetate), various starches, corn products, pectin, alkoxylated celluloses, polyesters, polyethers, proteins, nucleic acids, albumin, gelatin, pullulan, chitin, chitosan, agar, starch, collagen, dextran and modified dextrans, polysaccharides, polylactide/polyglycolide, polyalkylcyanoacrylates, polyacrylamide, polysorbates, polyethylene ethers, polyethylene esters, polyoxyethylene/polyoxypropylene block polymers, cellulose acetophthalate, hydroxypropylmethyl cellulose, cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, cellulose acetate butyrate, methyl cellulose, ethyl cellulose, hydroxyethyl cellulose, propyl cellulose, hydroxypropyl cellulose, hydroxypropyl methyl cellulose (hypromellose), lower-substituted hydroxypropyl cellulose, carboxymethyl cellulose, and mixtures thereof.

10. The capsule according to claim 9, wherein the sealed two-piece capsule is an acid-resistant capsule or an immediate release capsule.

11. The capsule according to claim 9, wherein the sealed two-piece capsule further comprises a pharmaceutical ingredient.

12. The capsule according to claim 9, wherein the sealed two-piece capsule further comprises a nutraceutical, a nutritional supplement, or a mixture thereof.

13. The capsule according to claim 9, wherein the acid resistant band further comprises rosin.

14. The sealed two-piece capsule according to claim 9, wherein the corn product is amaizo, amylose, zein, or any combination thereof.

15. A method comprising orally administering to a human or an animal the sealed two-piece capsule of claim 9.

* * * * *